United States Patent [19]

Kato et al.

[11] Patent Number: 5,033,013
[45] Date of Patent: Jul. 16, 1991

[54] METHOD AND APPARATUS FOR MEASURING THE AMOUNT OF EXERCISE

[75] Inventors: Yasuji Kato; Hiroyuki Kobayashi, both of Tokyo, Japan

[73] Assignee: Yamasa Tokei Meter Co., Ltd., Japan

[21] Appl. No.: 522,945

[22] Filed: May 14, 1990

Related U.S. Application Data

[63] Continuation-in-part of Ser. No. 115,943, Nov. 2, 1987, abandoned.

[30] Foreign Application Priority Data

| Apr. 22, 1985 | [JP] | Japan | 60-59963[U] |
| Apr. 22, 1985 | [JP] | Japan | 60-85970 |

[51] Int. Cl.$^5$ .............................................. G01C 22/00
[52] U.S. Cl. .................................... 364/561; 235/105; 364/565; 364/413.01
[58] Field of Search ............... 364/565, 561, 556, 415, 364/413.01, 410, 143, 413.29; 340/323 R; 324/171, 168; 235/105; 36/136.1, 44, 72 B; 272/69, 70

[56] References Cited

U.S. PATENT DOCUMENTS

| 2,882,244 | 4/1959 | Milton . | |
| 3,702,886 | 11/1972 | Argauer et al. . | |
| 4,100,401 | 7/1978 | Tutt et al. | 368/10 X |
| 4,192,000 | 3/1980 | Lipsey | 364/413.29 |
| 4,285,041 | 8/1981 | Smith | 364/415 |
| 4,322,609 | 3/1982 | Kato | 235/105 |
| 4,371,945 | 2/1983 | Karr et al. | 235/105 X |
| 4,387,437 | 6/1983 | Lowrey et al. | 364/561 |
| 4,402,147 | 9/1983 | Wu | 235/105 X |
| 4,460,823 | 7/1984 | Ruehlemann | 235/105 |
| 4,466,204 | 8/1984 | Wu | 235/105 X |
| 4,510,704 | 4/1985 | Johnson | 235/105 X |
| 4,525,074 | 6/1985 | Murakami | 368/10 |
| 4,560,861 | 12/1985 | Kato et al. | 235/105 |
| 4,560,928 | 12/1985 | Hayward | 324/172 |
| 4,578,769 | 3/1986 | Frederick | 364/565 |
| 4,703,445 | 10/1987 | Dassler | 364/561 |
| 4,771,394 | 9/1988 | Cavanagh | 364/561 |
| 4,962,469 | 10/1990 | Ono et al. | 364/561 |

FOREIGN PATENT DOCUMENTS 0115154 4/1980 Japan .

Primary Examiner—Parshotam S. Lall
Assistant Examiner—S. A. Melnick
Attorney, Agent, or Firm—Lowe, Price, LeBlanc & Becker

[57] ABSTRACT

A method and apparatus for accurately measuring an amount of exercise taken by a walker in terms of a walking speed, the distance traveled and the energy consumed. Impacts made by contacts of a foot of the walker with the ground are detected by a detector so as to produce corresponding contact signals. The number of the contact signals in a predetermined unit of time is counted by a processor to obtain a pitch in the unit of time, and a stride of the walker is calculated from said pitch and the height of the walker by the processor according to a predetermined empirical relationship of $ST = (0.1688 \times HT)/(1 - 0.0174 \times PI \times HT)$, where ST is the stride in meters, PI is the pitch in number of steps every 10 seconds, and HT is the walker's height in meters. The data on said height are inputted to the processor beforehand. Then the stride is multiplied by the pitch, to obtain and display a walking speed of the walker in said unit of time. The energy, e.g., in terms of calories consumed by the walker, is measured by the method of the present invention, utilizing an empirical relationship of $C = (0.0005 \times PI \times WT)$ (when $PI \leq 15$) or $C = (0.0013 \times PI - 0.0126) \times WT$ (when $PI > 15$), where C is the consumed energy in kcal in 10 seconds, PI is the pitch in number of steps every 10 seconds, and WT is the bodyweight of the walker in kg.

12 Claims, 10 Drawing Sheets (1)

(2)

(3)

(4)

METHOD AND APPARATUS FOR MEASURING THE AMOUNT OF EXERCISE

CROSS REFERENCE TO RELATED APPLICATION

This application is a Continuation-in-Part of U.S. application Ser. No. 115,943 filed on Nov. 2, 1987 now abandoned.

BACKGROUND OF THE INVENTION

I. Field of the Invention

This invention relates to a method and apparatus for measuring an amount of exercise. More particularly, this invention relates to a method and apparatus for measuring an amount of exercise of a walker in terms of speed of the walker, traveling distance or in terms of consumed energy in calories.

II. Description of the Prior Art

As disclosed in U.S. Pat. No. 4,578,769, such an exercise determination involves detection of a time t for which a foot of a runner comes into contact with the ground. On the basis of the time t, speed v, mileage l and consumed calories E are then calculated from the following empirical formulae:

$$v = -1.46 + 41.5 \times t$$

$$l = vT$$

$$E = 0.98 \times W \times l$$

wherein T is the elapsed time, and W is the weight of a runner.

However, the known method has a disadvantage in that it is not possible to determine the number of steps taken in walking or running, because it is designed to detect a time length for which the foot of a runner or jogger is in contact with the ground, so that the speed v may not be accurately calculated.

SUMMARY OF THE INVENTION

Accordingly, an object of the present invention is to provide a method and apparatus for measuring accurately an amount of exercise in terms of the speed of a walker, the distance traveled and the energy consumed in calories.

In one aspect of the present invention, there is provided a method of measuring a walking speed of a walker. In this method, impacts made by the contacts of a foot of the walker with the ground are detected by a detector so as to produce corresponding contact signals. The number of the contact signals in a predetermined unit of time is counted by processing means to obtain a pitch in said unit of time. Then the stride of the walker is calculated from said pitch and the known height of the walker by the processing means according to a predetermined empirical relationship. The empirical relationship is represented by the following equations:

$$ST = (0.1688 \times HT)/(1 - 0.0174 \times PI \times HT),$$

where
ST is the stride in meters,
PI is the pitch in number of steps every 10 seconds, and
HT is the walker's height in meters.
It should be noted that the unit of time corresponding to the empirically determined numerical constants in the expression for ST cited above is 10 seconds. The data on said height are inputted to the processing means beforehand. Then the stride is multiplied by the pitch, to obtain a walking speed of the walker in said unit of time, e.g., in meters per every 10 seconds in the given example. The thus obtained speed of the walker in said unit of time is then conveniently displayed on a display.

In a second aspect of the present invention, there is provided a method of measuring distance travelled by a walker in a unit of time. This method comprises the same steps as in the previously described method of measuring a walking speed of a walker according to the first aspect of the present invention, and further comprises the step of multiplying the walking speed by said unit of time after the walking speed is calculated to obtain the distance travelled by the walker in said unit of time. The obtained distance is then displayed on a display.

According to a third aspect of the present invention, a method of measuring a cumulative distance travelled by a walker is provided. This method comprises the same steps as the described method of measuring the distance travelled by a walker according to the second aspect of the present invention, and further comprises the step of integrating the distance travelled by the walker in said unit of time to obtain cumulative distance travelled by the walker. The thus obtained distance is then displayed on a display.

According to a fourth aspect of the present invention, there is provided a method of measuring an amount of exercise in terms of calories of energy consumed by a walker in the unit of time. In this method, the pitch of the contacts of the foot of the walker is obtained in the same manner as in the previously described methods. The energy in terms of calories consumed by the walker in the chosen unit of time is then calculated from the calculated pitch and weight of the walker according to other predetermined empirical relationships. The relationships are represented by the following equations:

$$C = (0.0005 \times PI \times WT) \text{ (when } PI \leq 15)$$

$$C = (0.0013 \times PI - 0.0126) \times WT \text{ (when } PI > 15)$$

where
C is the consumed energy in kcal in 10 seconds,
PI is the pitch in number of steps every 10 seconds, and
WT is the bodyweight of the walker in kg.
The weight is provided to the processing means beforehand. Then the thus obtained calories consumed are displayed by a display.

According to a fifth aspect of the present invention, there is provided a method of measuring an amount of exercise in terms of calories of cumulative energy consumed by a walker in a selected session of walking. This method comprises the same steps as in the described method of measuring the amount of exercise in terms of calories of energy consumed by a walker in the chosen unit of time according to the fourth aspect of the present invention, and further comprises the step of integrating the calories consumed in said unit of time over time through the entire walking time to obtain a cumulative consumed calories. The obtained cumulative calories consumed are then displayed on a display.

In another aspect of the present invention, there is provided apparatus for carrying out the above-described methods of the present invention. The apparatus comprises a detector for detecting impacts made by the contacts of a foot of the walker with the ground to produce corresponding contact signals, means for processing the detected signals and means for providing a display. In the processing means, the above-mentioned empirical relationships, as well as other necessary information such as the height or weight of the walker are inputted beforehand, and the calculations mentioned in the steps of the methods of the present invention are carried out by the processing means.

According to the present invention, the amount of exercise in terms of speed of the walker, traveling distance and the calories consumed may be accurately measured and displayed.

DETAILED DESCRIPTION OF THE PREFERRED EMBODIMENTS

The term "walker" used in this specification and appended claims means not only literally a walking person but also includes a jogger and a runner. Similarly, the term "walking" or "walk" not only means its literal meaning, but also means jogging and running.

As mentioned above, in the first aspect of the present invention, there is provided a method of measuring a walking speed of a walker.

In this method, impacts made by the contacts of a foot of the walker with the ground are detected by a detector so as to produce corresponding contact signals. The impacts may be detected by a detector which will be described later in detail.

The number of the contact signals in a predetermined unit of time is counted by processing means to obtain a pitch in a selected unit of time.

Then the stride of the walker from said pitch and the height of the walker is calculated by the processing means according to a predetermined empirical relationship. The empirical relationship according to this invention, as determined by careful experiments is represented by the following equation [I]:

$$ST = (0.1688 \times HT)/(1 - 0.0174 \times PI \times HT) \qquad [I]$$

where
ST is the stride in meters,
PI is the pitch in number of steps every 10 seconds, and
HT is the walker's height in meters.
The data on said height are inputted to the processing means beforehand.

This relationship was obtained empirically by conducting the experiments described below, prior to which the following was known in the art:

1) The speed of walking (SP) is determined by the stride (i.e., length of a stride) (ST) and the pitch (PI). That is, $SP = ST \times PI$ 2) The stride is influenced by the speed, pitch and height of the walker.

Figure 1:
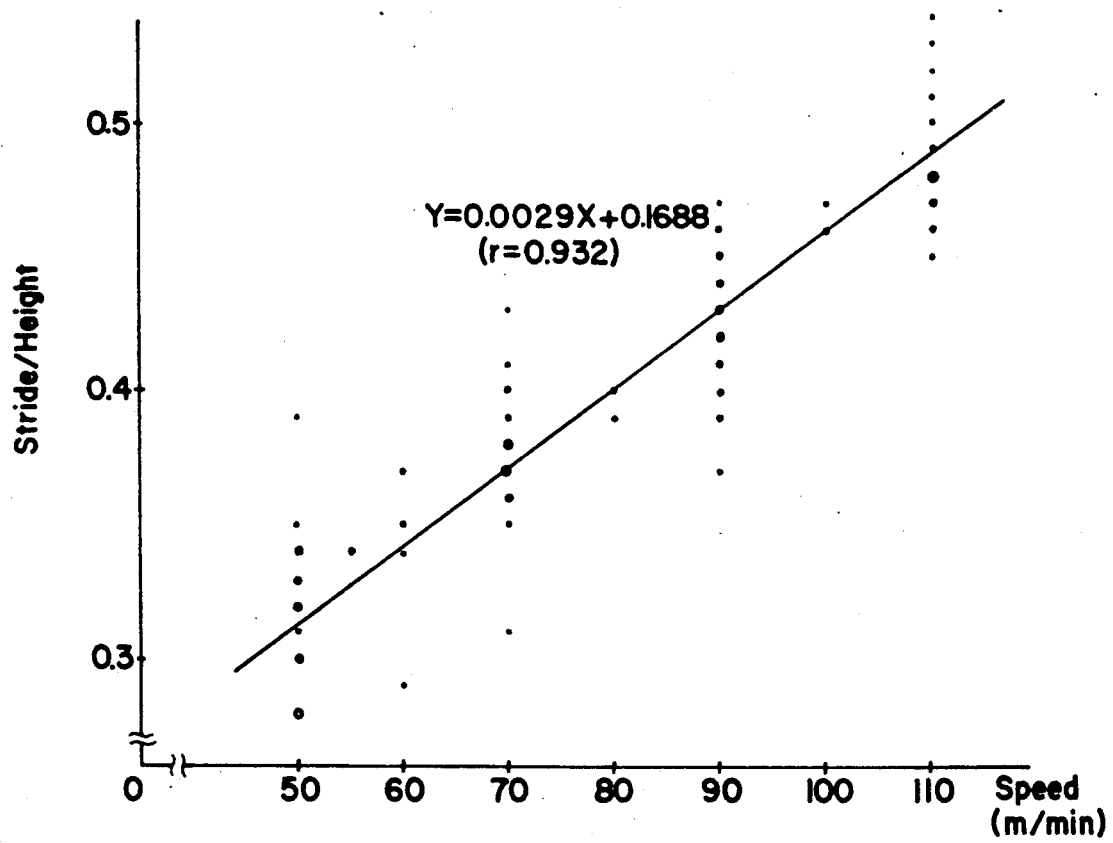
FIG. 1 graphically shows the relationship between stride/height and speed obtained empirically by conducting experiments.

Bearing in mind this knowledge, the following experiments were conducted:

One hundred and forty two persons were made to walk on a treadmill at a speed of 50-110 m/min. The pitch (PI) and stride (ST) of the walking, as well as the heights of the walkers (HT) were measured. The relationship between ST/HT and SP was plotted taking ST/HT along the ordinate and SP along the abscissa. The results are shown in FIG. 1. As shown in FIG. 1, with a high correlation ($r = 0.932$), the following relationship was obtained:

$$ST/HT = 0.0174 \times SP + 0.1688 \qquad \text{i)}$$

It should be noted that in FIG. 1, the slope is 0.0029 (i.e., 1/6 of 0.0174) because the pitch is expressed in terms of number of steps per 1 minute while in equation [I], pitch is expressed in terms of steps per 10 seconds. By inserting the relationship of $SP = ST \times PI$ into the above equation i), the equation [I] was obtained.

Then the stride is multiplied by the pitch, to obtain a walking speed of the walker in said unit of time.

All of the above calculations may be conducted in the processing means. The program of the calculations may easily be prepared by those skilled in the art.

The thus obtained walking speed is displayed in a display operationally connected to the processing means. The method of displaying the data processed by the processing means is well-known in the art.

As mentioned earlier, in the second aspect of the present invention, there is provided a method of measuring distance travelled by a walker in a unit of time. This method comprises the same steps as in the method of measuring walking speed of a walker according to the first aspect of the present invention, and further comprises the step of multiplying the walking speed by said unit of time after the walking speed is calculated to obtain the distance travelled by the walker in said unit of time. Needless to say, this calculation is also most conveniently carried out by the processing means. The obtained distance is then displayed on a display.

According to the third aspect of the present invention, a method of measuring a cumulative distance travelled by a walker is provided. This method comprises the same steps as the method of measuring the distance travelled by a walker according to the second aspect of the present invention, and further comprises the step of integrating the distance travelled by the walker in said unit of time for the entire session of walking to obtain the corresponding cumulative distance travelled by the walker. This calculation is also carried out by the processing means. The thus obtained distance is then displayed on a display. By this method, even when the walker is on the way to his or her destination, the distance travelled at any intermediate time during the journey can be known. Needless to say, after the walker reached his or her destination, the total distance travelled from the starting point to the destination can also be known.

According to the fourth aspect of the present invention, a method of measuring an amount of exercise in terms of calories of energy consumed by a walker is provided. In this method, the pitch of the contacts of the foot of the walker is obtained in the same manner as in the methods according to the first to third aspect of the present invention. The energy in terms of calories consumed by the walker in said unit of time is then calculated from said pitch and the weight of the walker according to a predetermined empirical relationship. The relationship is represented by the following equations [II] and [III]:

$$C = (0.0005 \times PI \times WT) \text{ (when } PI \leq 15) \quad [II]$$

$$C = (0.0013 \times PI - 0.0126) \times WT \text{ (when } PI > 15) \quad [III]$$

where
C is the consumed energy in kcal in 10 seconds,
PI is the pitch in number of steps every 10 seconds, and
WT is the bodyweight of the walker in kg.
This relationship was obtained empirically by conducting the experiments described below, prior to which the following was known in the art:

1) The energy demand in walking is determined by the speed and the bodyweight of the walker.

2) The speed of walking (SP) is determined by the stride (i.e., length of a stride) (ST) and the pitch (PI). That is, $SP = ST \times PI$ 3) The oxygen demand is not much increased by enlarging the stride, but is sharply increased by increasing the pitch. This is because an increase in the pitch requires a rapid compression of the walker's muscles.

Figure 2:
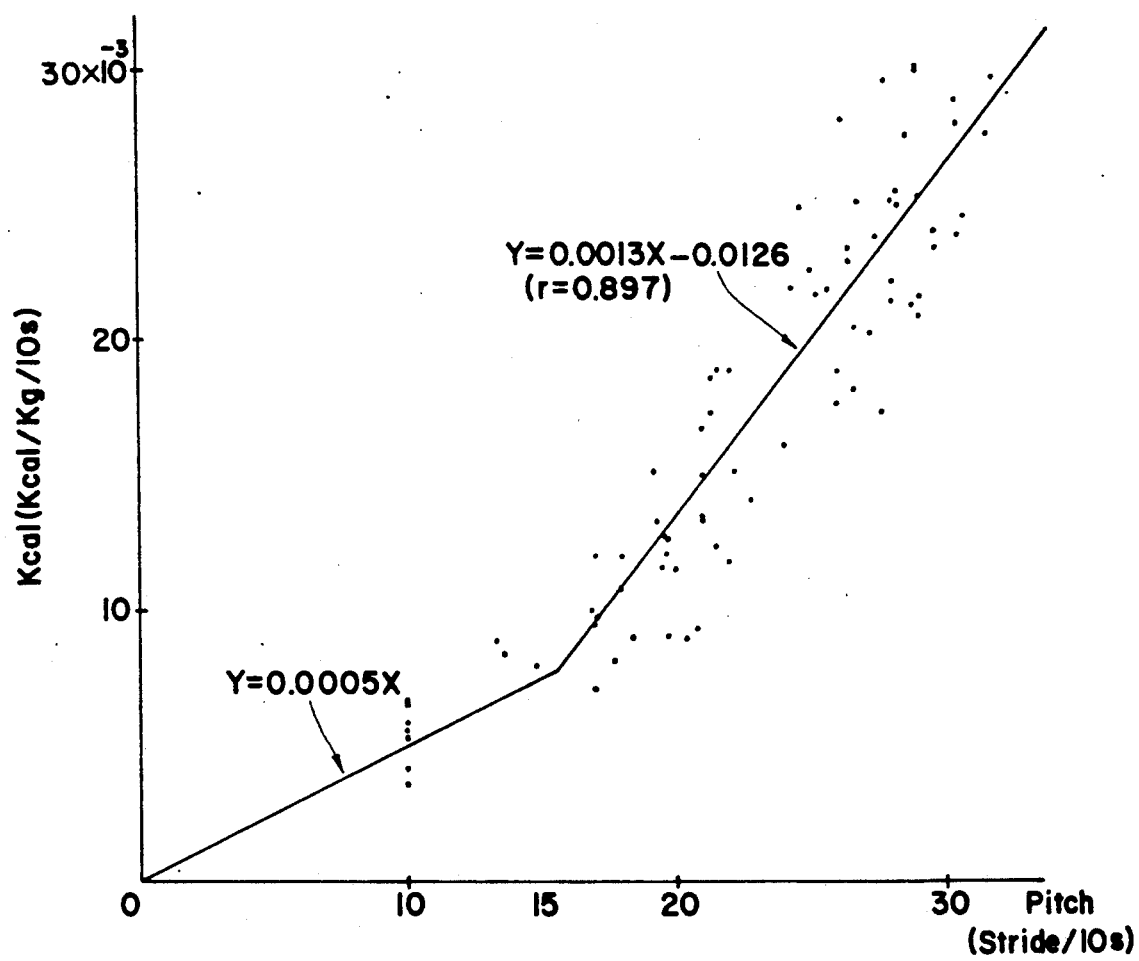
FIG. 2 graphically shows the relationship between pitch and consumed calories obtained empirically by conducting experiments.

4) The consumed calories per bodyweight (C/W) (kcal/kg) is obtained by $$C/W = VO_2 \times 4.99 \quad \text{ii)}$$

wherein $VO_2$ is the oxygen consumption. Bearing in mind the knowledge per 1) to 4), the following experiments were performed:

Seventy three persons were made to walk and run on a treadmill at a speed of 50–110 m/min and 100–220 m/min. The pitch (PI) and oxygen consumption ($VO_2$), as well as the bodyweight of the walkers (W), were measured. The consumed calories per bodyweight (C/W) was calculated from the above-described equation ii). The relationship between C/W and PI was plotted taking C/W along the ordinate and PI along the abscissa. The results are shown in FIG. 2. As shown in FIG. 2, with a high correlation (r =0.897), the following relationship was obtained:

$$C/W = 0.0013 \times PI - 0.0126 \quad \text{iii)}$$

By multiplying the equation with the bodyweight, equation [III] was obtained. It should be noted that the average and the standard deviation of the pitch in equation [III] were as follows:
Average of Pitch: 23.9 (number of steps/10 seconds)
Standard Deviation: ±4.78
Thus, from the distribution, 90% of the pitch is included in the range of 15.6–32.4. To obtain an equation by which the consumed calories when the pitch is less than 16 may be obtained, the C/W per single step was measured. As a result, the C/W per step was determined to be 0.0005 kcal/kg/step.

$$C/W/\text{step} = 0.0005 \quad \text{iv)}$$

By multiplying equation iv) with the bodyweight and the pitch, equation [II] was obtained, as shown in FIG. 2.

The data of the walker's bodyweight are provided to the processing means beforehand. Then the thus obtained calories consumed in the unit time are displayed by a display.

According to the fifth aspect of the present invention, a method of measuring an amount of exercise in terms of calories of cumulative energy consumed by a walker is provided. This method comprises the same steps as in the method of measuring the amount of exercise in terms of calories of energy consumed by a walker in the unit time according to the fourth aspect of the present invention, and further comprises the step of integrating the calories consumed in said unit of time over time through the entire walking time to obtain a cumulative figure for the consumed calories. This calculation is also conducted by the processing means. The obtained cumulative consumed energy is then displayed on a display. By this method, even when the walker is on the way to his or her destination, the calories consumed within an intermediate time can be known. Likewise, after the walker reached his or her destination, the total calories consumed during the walking from the starting point to the destination can also be known.

In another aspect of the present invention, there is provided apparatus for carrying out the above-described methods of the present invention. The apparatus comprises a detector for detecting impacts made by the contacts of a foot of the walker with the ground to produce corresponding contact signals, processing means and a display.

A preferred embodiment of the apparatus for measuring the amount of exercise of the present invention will now be described referring to FIGS. 3 and 4.

Figure 3:
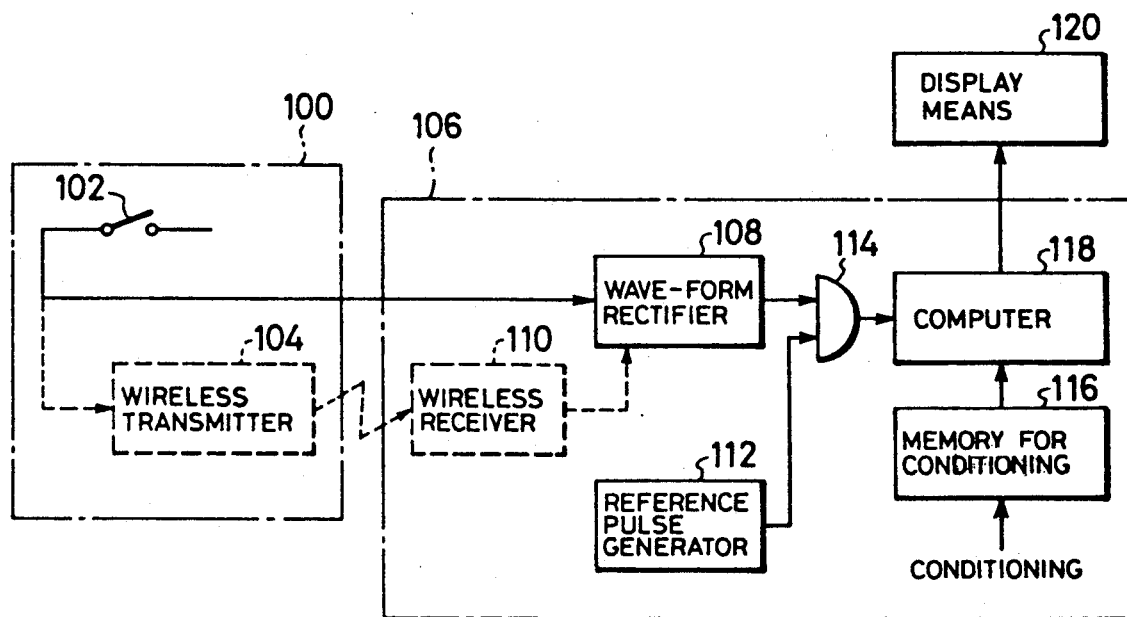
FIG. 3 is a block diagram showing a preferred embodiment of the measuring apparatus of the present invention.

FIG. 3 is a block diagram illustrating a preferred embodiment of the apparatus according to the present invention. The apparatus comprises a detector generally indicated by the reference numeral 100, processing means generally indicated by the reference numeral 106 and a display means 120 of known type.

The detector 100 includes a switch 102 defining a detector element designed to detect impacts made by the contacts of the foot of a walker with the ground, i.e., the steps of the walker. The resulting contact signals are transmitted to a wave-form rectifier 108 with a transmission circuit directly or, optionally, through a transmitter 104 attached to the detector 100 by way of a wireless receiver 110 attached to the processing means 106.

The processing means 106 includes a wave-form rectifier 108; receiver 110 which may be used, if required; a reference pulse generator 112; an AND circuit for receiving therein a signal transmitted from the rectifier 108 and the generator 112; and an operation processor 118 for receiving therein a pulse processed in the circuit 114. The processor 118 also receives the empirical above-described calculation formulae and date on the height and bodyweight of the walker previously stored in a condition-setting memory 116, for comparison and calculation purposes and then transmits a variety of the resulting processed values to the display 120.

According to the described method for determining the amount of exercise with such apparatus, the switch 102 of the detector 100 first detects the impacts given by the contacts of the foot of the walker with the ground, i.e., the steps of the walker, and contact signals are produced. The resulting contact signals of a wave-form as shown in FIG. 4(2) are sent to the wave-form rectifier 108 of the processing means 106.

As shown in FIG. 3 by a solid line, the contact signals may be sent directly to the wave-form rectifier 108. Alternatively, they may be transmitted thereto from the radio frequency transmitter 104 of the detector 100 by way of the radio frequency receiver 110 of processing means 106, as shown in FIG. 3 by a dotted line.

Figure 4:
FIG. 4 is a waveform diagram of signals in the block diagram of FIG. 3.
Figure 4:
Figure 4:
Figure 4:

The contact signals sent to the wave-form rectifier 108 are rectified there to a rectangular wave as shown in FIG. 4(3), and this is in turn sent to the AND circuit 114 of processing means 106 along with a reference pulse, shown in FIG. 4(1), which is generated from the reference pulse generator 112 of processing means 106.

The rectangular wave and reference pulse are then processed in the AND circuit 114, and are sent to the operation processor 118 of processing means 106 in the form of a pulse as shown in FIG. 4(4).

In the operation processor 118, the pulse sent thereto is processed as described above, and the speed, cumulative traveling distance or the cumulative calories consumed may be calculated by the computer 118. The resulting value is sent to the display 120 and is displayed thereby.

One embodiment of a shoe having the aforesaid apparatus incorporated therein will now be explained with reference to FIGS. 5 to 7.

Figure 5:
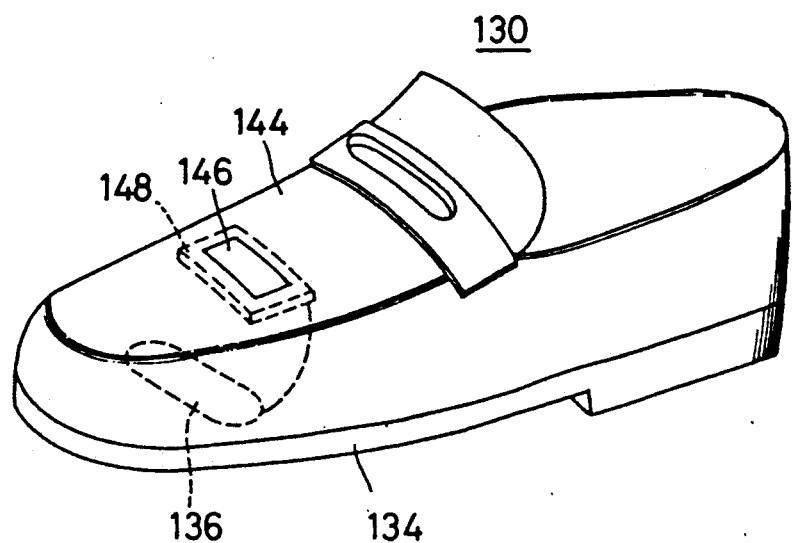
FIGS. 5-7 show one embodiment of a shoe into which the measuring apparatus of the present invention is incorporated, FIG. 5 being a perspective view of that shoe, FIG. 6 being a plan view of that shoe, and FIG. 7 being a sectional view taken along the line 7—7 in FIG. 6.
Figure 6:
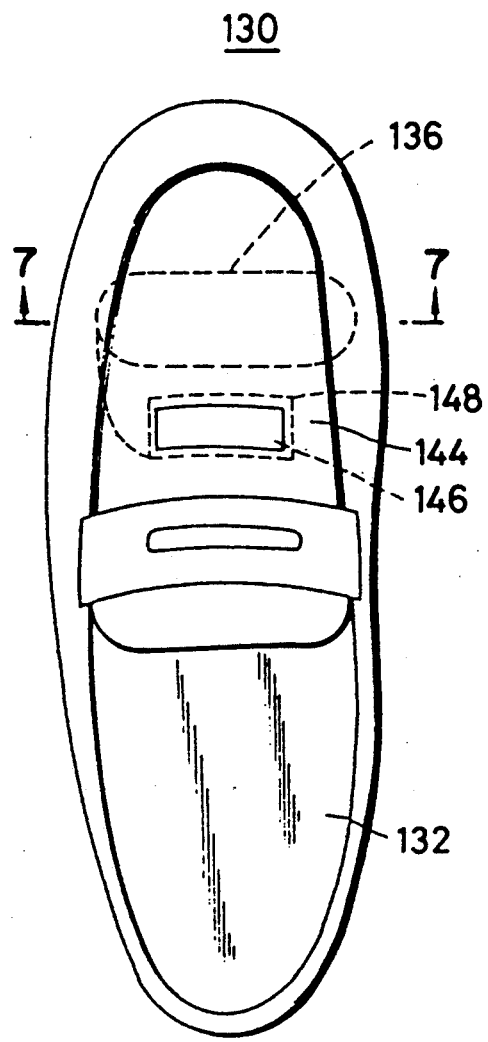
Figure 7:
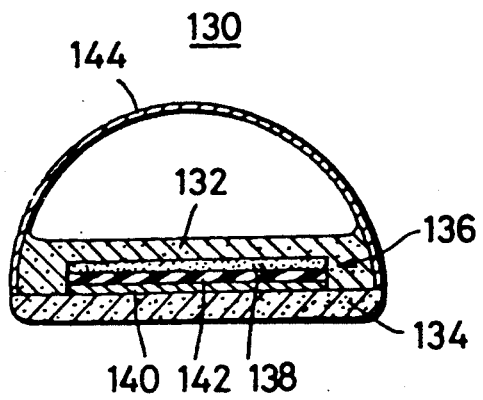

FIG. 5 is a perspective view of a shoe, FIG. 6 is a plan view of the shoe, and FIG. 7 is a sectional view taken along the line 7—7 in FIG. 6. A shoe generally indicated by reference numeral 130 includes an insole 132 and a sole 134, and a big toe portion located therebetween. The big toe portion is provided with a press switch 136 which is one example of the switch of the detector for detecting the impacts given by the contacts of the foot with the ground to send out contact signals.

As illustrated in FIG. 7, the switch 136 comprises a pressure-conductive rubber element 142 fixedly interposed between a pair of electrodes formed by a bundle of fine copper wires 138 and an electrically conductive film substrate 140. Pressure-conductive rubber is a well-known rubber which is changed to become electrically conductive when a predetermined pressure is applied thereto, and is commercially available from, for example, Bridgestone of Tokyo, Japan. Due to a load applied on the foot, conduction is made between the bundle of the fine copper wires 138 and the film substrate 140 via the pressure-conductive rubber 142, so that a current providing the contact signals flows.

The shoe 130 is provided on its instep 144 with a processor-display combination 148 wherein a microprocessor serving as processing means is integral with a display 146 using a liquid crystal, etc. The current acting as the contact signals is sent to the processor-display combination 148 to measure the number of steps per unit time. The above-described calculations are made by the microprocessor and the resulting speed in the unit time, the traveling distance in the unit time, the cumulative traveling distance, the calories consumed in the unit time, or the cumulative consumed calories are then displayed on the display 146.

Figure 8:
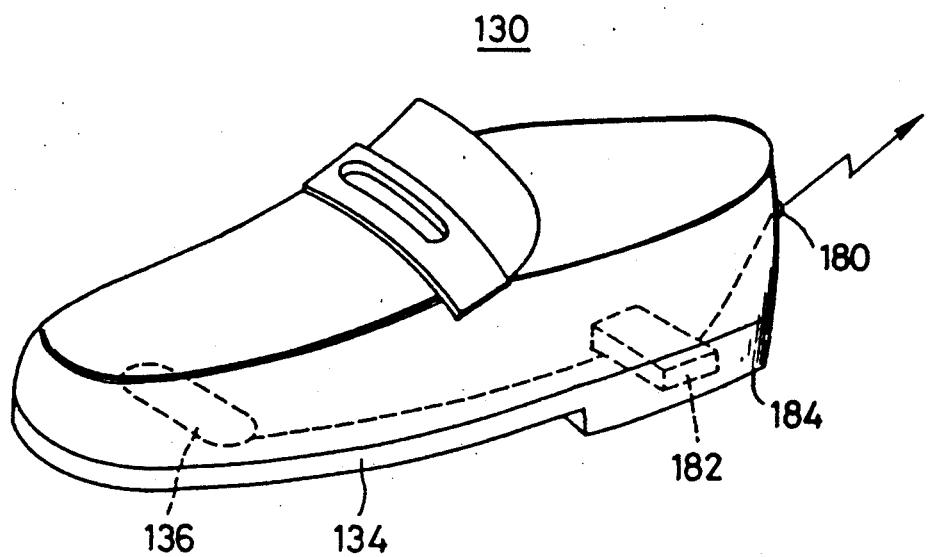
FIG. 8 is a perspective view of a shoe showing another embodiment, wherein the apparatus of the present invention is separately provided in that shoe.

FIG. 8 shows another embodiment of the measuring apparatus of the present invention, which is shown to be mounted on a shoe. In addition to a press switch 136, a shoe 130 includes in, for instance, its heel portion 184 a radio frequency transmitter 182 having a transmitting portion 180 for transmitting the contact signals. In this embodiment, with the signals transmitted from the transmitter 182, the amount of exercise can be measured by a separately provided processor-display combination wherein a display 120 is integral with processing means 160 illustrated in FIG. 3 and provided with a receiver 110, the combination being designed to be carried or held by either the walker or by another person.

A description will now be provided of an embodiment of the portable measuring apparatus of the present invention, which is attachable to the waist of a walker.

Figure 9:
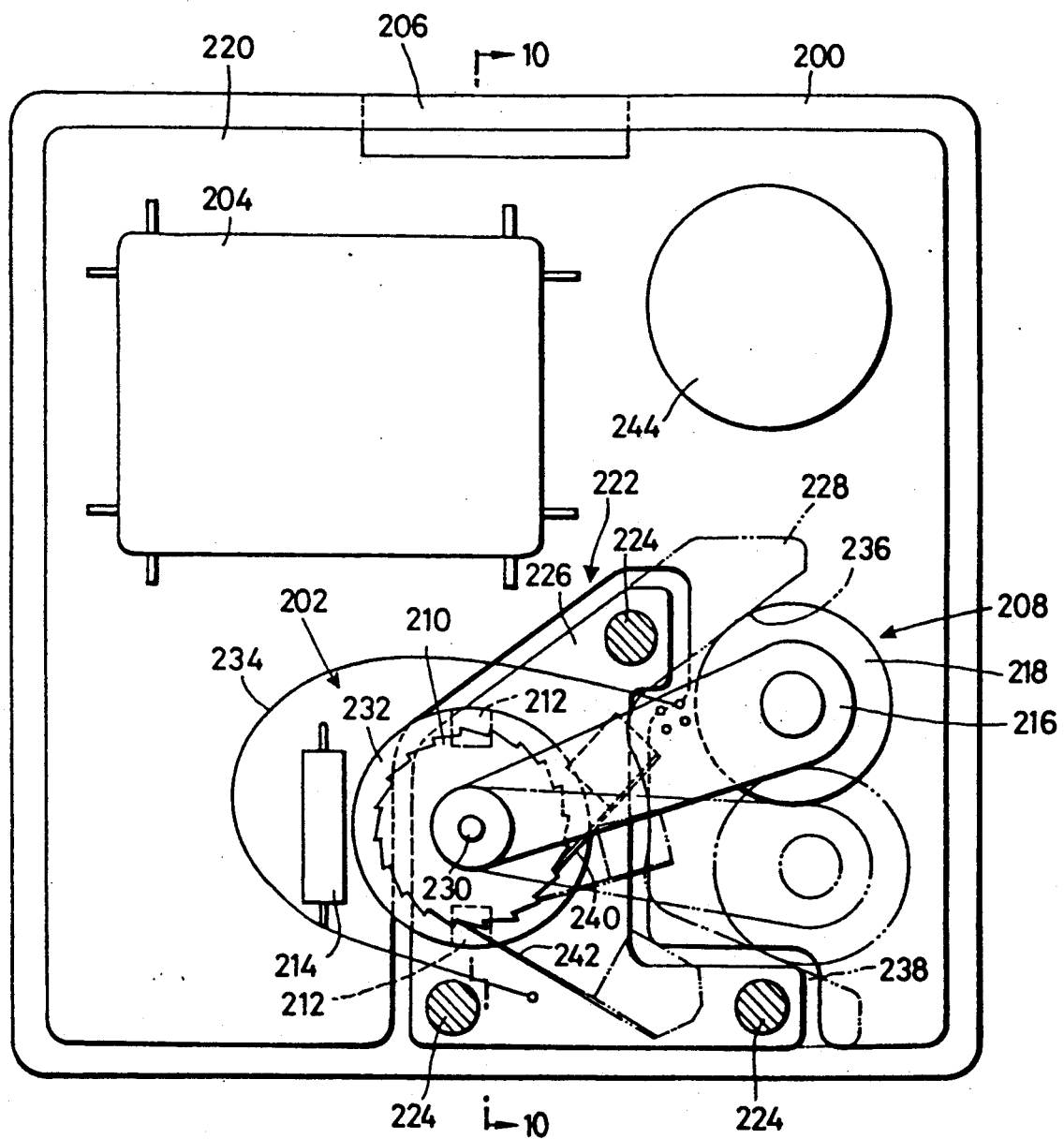
FIGS. 9 and 10 show another embodiment of the portable measuring apparatus of the present invention, FIG. 9 being a front view showing the inner structure thereof, and FIG. 10 being a sectional view taken along the line 10—10 of FIG. 9.
Figure 10:
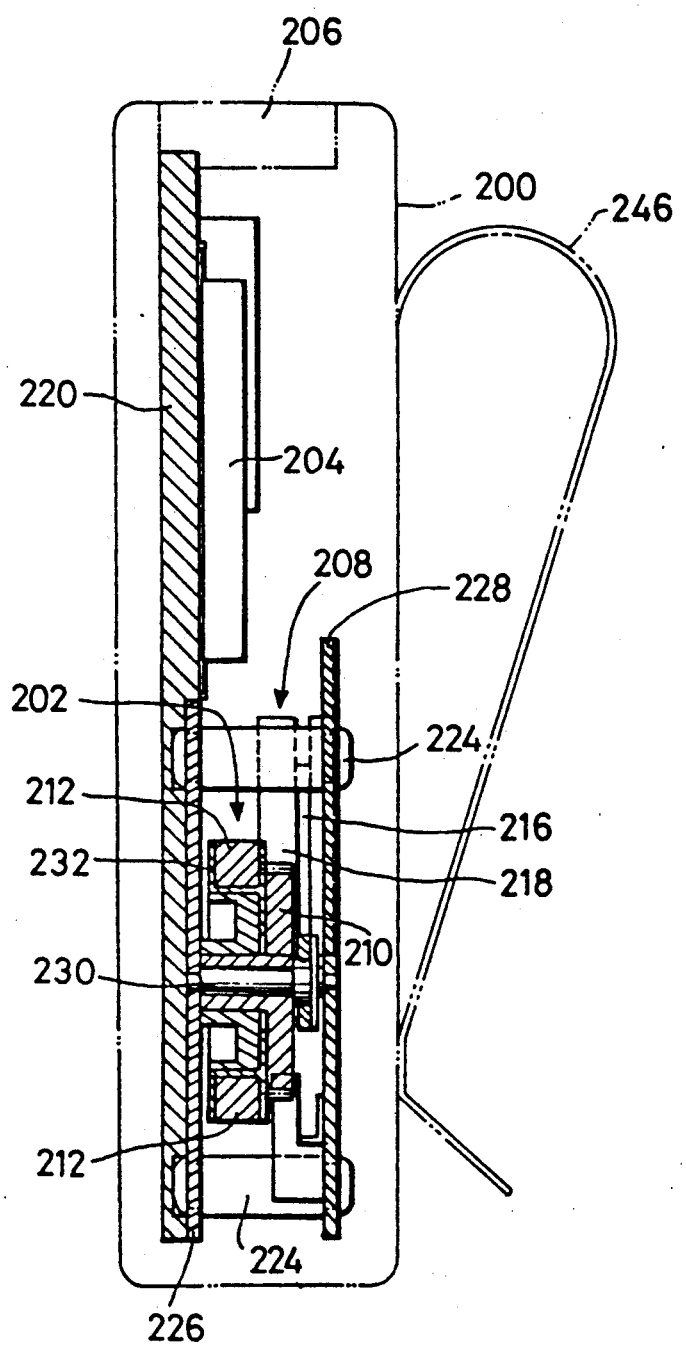

FIG. 9 is a front view of the inner structure of that embodiment, and FIG. 10 is a sectional view taken along the line 10—10 in FIG. 9.

The measuring apparatus according to the third embodiment of the apparatus of the present invention includes in casing 200 a detector 202 for sensing the impacts given by the contacts of the foot of a walker with the ground when he or she walks, and a processor 204 for calculating and data on various amounts of exercise in response to a contact signal transmitted from the detector 202, and has on the upper portion of the casing 200 a display 206 for displaying the various amounts of exercises.

The detector 202 corresponds to the detector 100 shown in FIG. 3, and includes a pendulum 208 swinging in response to contact signals, a ratchet gear 210 rotating in operable association with the pendulum, a magnet 212 rotating in unison with the ratchet gear 210 and a reed switch 214 opened and closed by the magnet 212.

The pendulum 208 includes an arm 216 and a weight 218 attached to one of the arm 216. A substrate 220 built in the casing 200 is provided on its lower portion with a support portion 222 for supporting the pendulum 208. The support portion 222 includes two supporting plates 226 and 228 which are spaced away from each other by pins 224. The supporting plate 226 is fixedly provided on the lower portion of the substrate 220. Between both supporting plates 226 and 228, there is a shaft 230 to which the other end of the arm 216 is rotatably supported. The shaft 230 also supports the ratchet gear 210 and a magnet holder 232 rotating in unison with the gear 210.

The pendulum 208 is locked at one end to the arm 216 and at the other end to the supporting plate 228, and is designed to be regulated in respect of its sensitivity by means of a spring 234 arranged to form a loop. To keep the width of swinging of the pendulum 208 constant, the supporting plate 228 is provided with stopper portions 236 and 238 on its lower and upper portions. Moreover, the arm 216 of pendulum 208 is provided with a feed pawl 240 for rotating the ratchet gear 210, making use of swinging thereof. On the other hand, the supporting plate 228 is provided with a pawl 242 for preventing reversal of the ratchet gear 210.

The magnetic holder 232 is provided on the outer periphery with the magnets 212 and 212 in a diametrically opposite direction. The reed switch 214 is disposed on the substrate 220 in the vicinity of the ratchet gear 210. The reed switch 214 has a contact (not illustrated) that is opened or closed in known manner by the magnets 212 and 212 of the holder 232 rotating in unison with the ratchet gear 210 to transmit a contact signal to the processor 204. The magnets 212 are disposed at an equal interval so as to allow the reed switch 214 to be actuated per every ten steps, for instance.

On the upper portion of the substrate 220, there are disposed the processor 204 equivalent to the processing means 106 shown in FIG. 3, and a battery 244 serving as the power source for the processor 204. For the processor 204, use may be made of a microprocessor or the like, which generates a timing reference pulse and calculates and stores the amount of exercise in terms of the walker's speed in the unit time, the traveling distance in the unit time, the cumulative traveling distance, the calories consumed in the unit time, or the cumulative consumed calories from the contact signals transmitted from the reed switch 214, according to the above-described equations.

The display 206 corresponds to the display 120 shown in FIG. 3. The display 206 may be of the liquid crystal type, and displays a variety of the amount of exercise stored in the processor 204. The reed switch 214, processor 204, battery 244 and display 206 are operably connected with one another via printed wirings of known type (not shown) on the substrate 220.

It is to be noted that the magnets 212 and 212 may be rotated synchronously with the ratchet gear 210, and may, for instance, be mounted directly on the ratchet gear 210 without using the magnet holder 232. It is also to be noted that the number of magnets 212 is not limited to two, and three or more magnets 212 may be mounted in place in a well-balanced state.

When the measuring apparatus of the present invention is attached to, for example, the waist of a user during use, the pendulum 208 swings in operative association with the impact which the feet receive upon coming into contact with the ground, thereby causing the ratchet gear 210 to be rotated by the feed pawl 240 and generating on or off operation of the contact of reed switch 214 by the magnets 212 turning synchronously with the rotation of the gear 210. In this manner, contact signals are produced, and they are transmitted to the processor 204, and the above-described processing is made therein. The obtained amounts are then displayed in the display 206.

Figure 11:
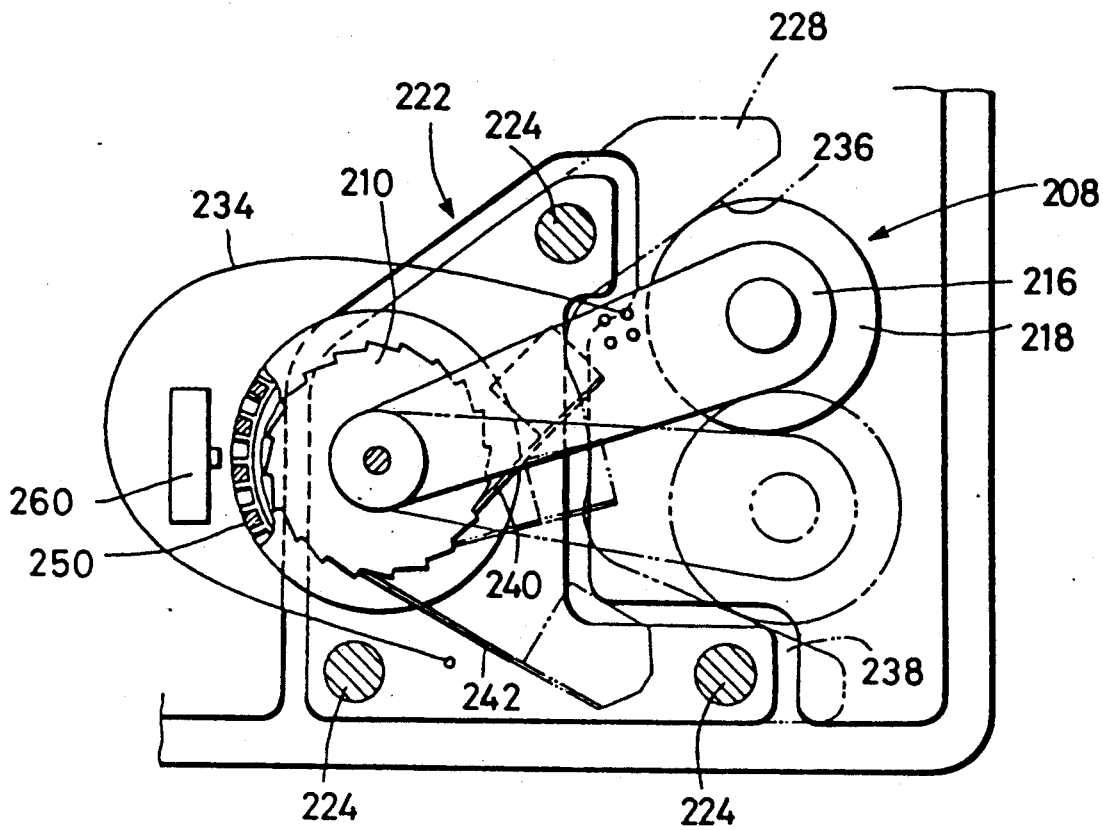
FIGS. 11 and 12 show another embodiment of the portable measuring apparatus of the present invention, FIG. 11 being a front view showing a part of the inner structure thereof, and FIG. 12 being an exploded perspective view showing a disk-like magnet utilized therein.
Figure 12:
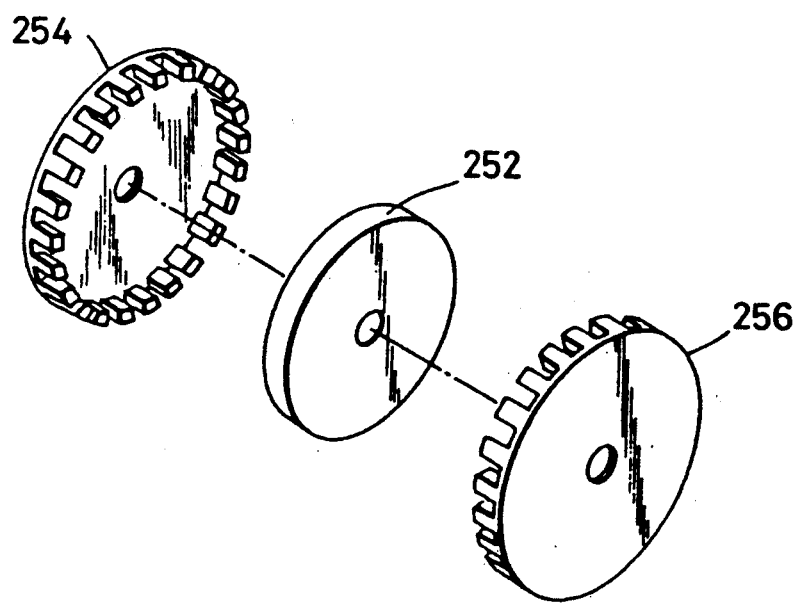

FIGS. 11 and 12 show a further embodiment of the portable measuring apparatus of the present invention. According to this embodiment, a disk magnet 250 including on its outer periphery an alternate arrangement of N- and S-pole plates is used in place of the magnet holder 232 and magnets 212 employed in the embodiment of FIGS. 9 and 10. The disk magnet 250 is designed to be rotated in unison with the ratchet gear 210, and its magnetism is sensed by means of a porcelain sensor 260 used in lieu of the reed switch 214 shown in FIG. 91 to send a contact signal to a processor.

The disk magnet 250 including a polar plate having on its circumference an alternate array of a number of N and S poles is obtained by fitting metal plates 254 and 256, each having on its circumference bent pieces defining pole pieces, over a disk-like magnet 252 and an S pole on the other side. As shown in FIG. 12, use of such a disk magnet 250 permits the porcelain sensor 260 to effect sophisticated detection, for instance the detection of each step.

Figure 13:
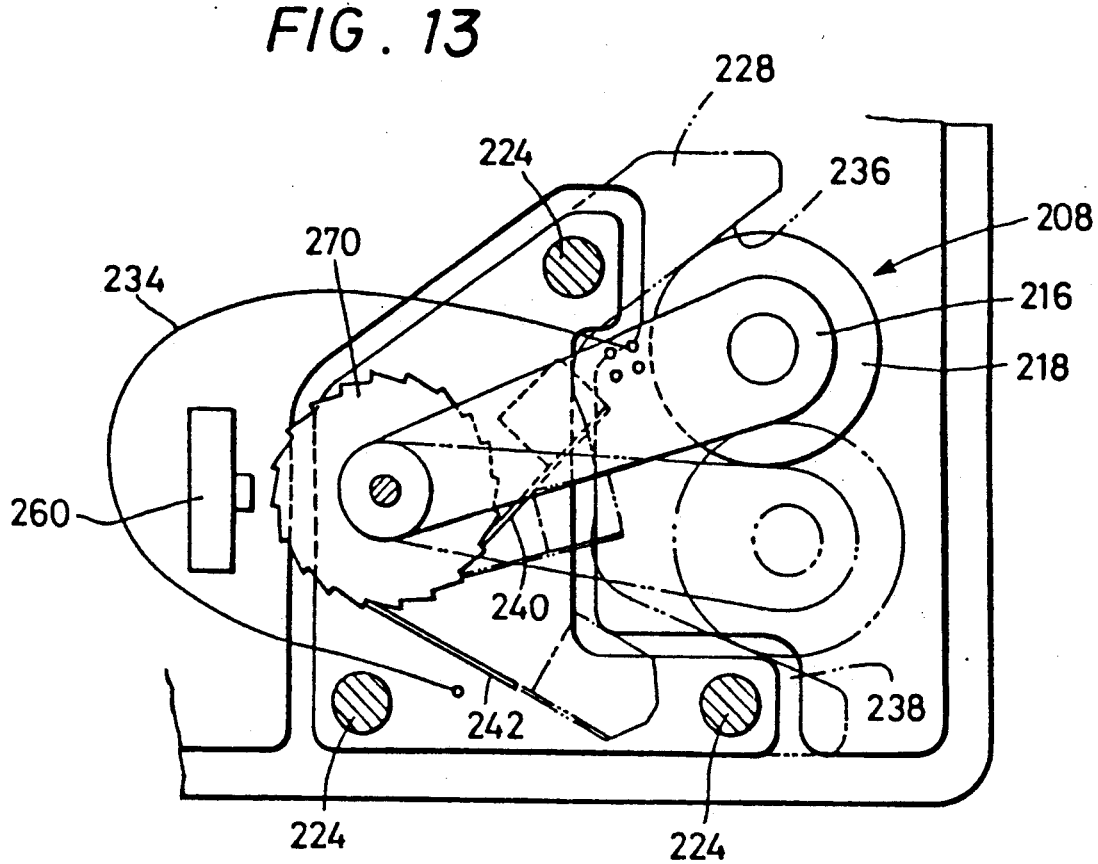
FIG. 13 is a front view showing a part of the inner structure of a still further embodiment of the portable measuring apparatus of the present invention.

FIG. 13 is a still further embodiment of the portable measuring apparatus of the present invention, wherein the ratchet gear 270 used is made of a metallic material that is also a magnetic material, without recourse to the magnets 212 and 250 used in the foregoing both embodiments, and its extremities are designed to be sensed by means of a porcelain sensor 260 to send the thus sensed signal to a processor 204. Even with this embodiment, detection of each step may be made.

Figure 14:
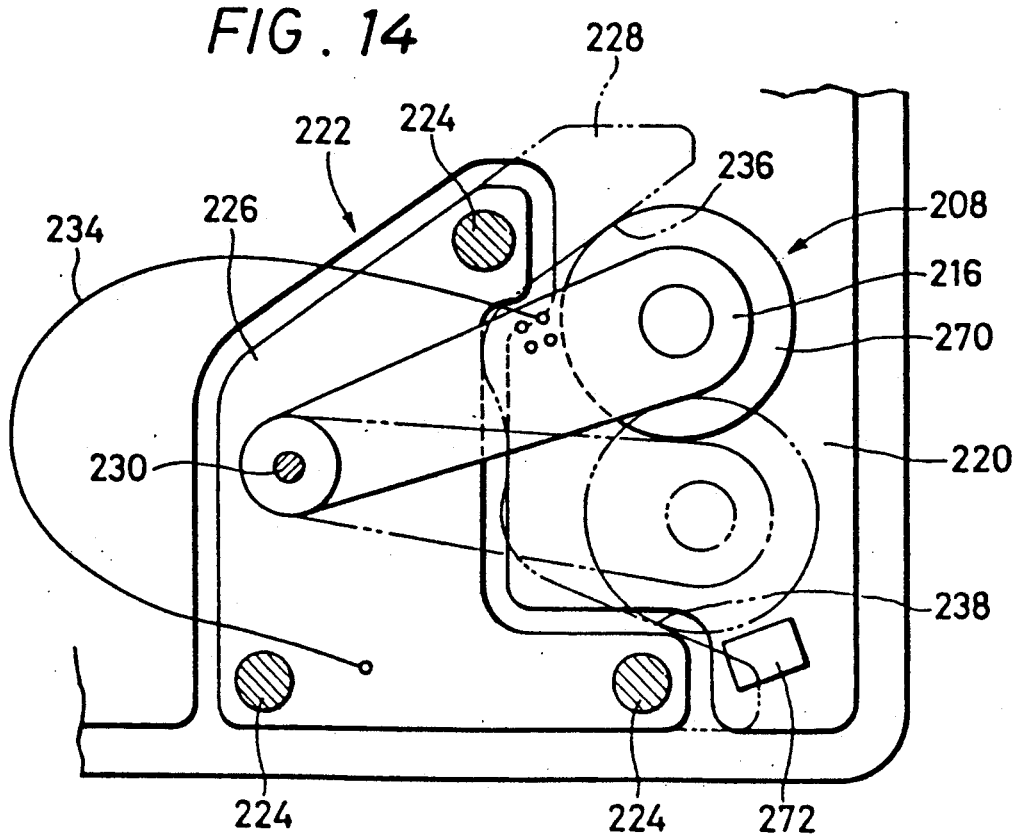
FIG. 14 is a front view showing a part of the inner structure of a still further embodiment of the portable measuring apparatus of the present invention.

FIG. 14 shows a still further embodiment of the measuring apparatus of the present invention, wherein the ratchet gear used in each of the foregoing three embodiments is omitted. A magnet 270, which also serves as a weight, is attached to one end of an arm 216 of a pendulum 208, and a reed switch or a magnetic sensor 272 is provided in the vicinity of a lower stopper portion 238 of a substrate 220. When the pendulum 208 swings down due to the vibration in response to the impacts given by the contacts of the foot with the ground, the magnet 270 is sensed by the reed switch or magnetic sensor 272 to transmit the resulting signals to a processor 204. In this manner, each step may be sensed.

Figure 15:
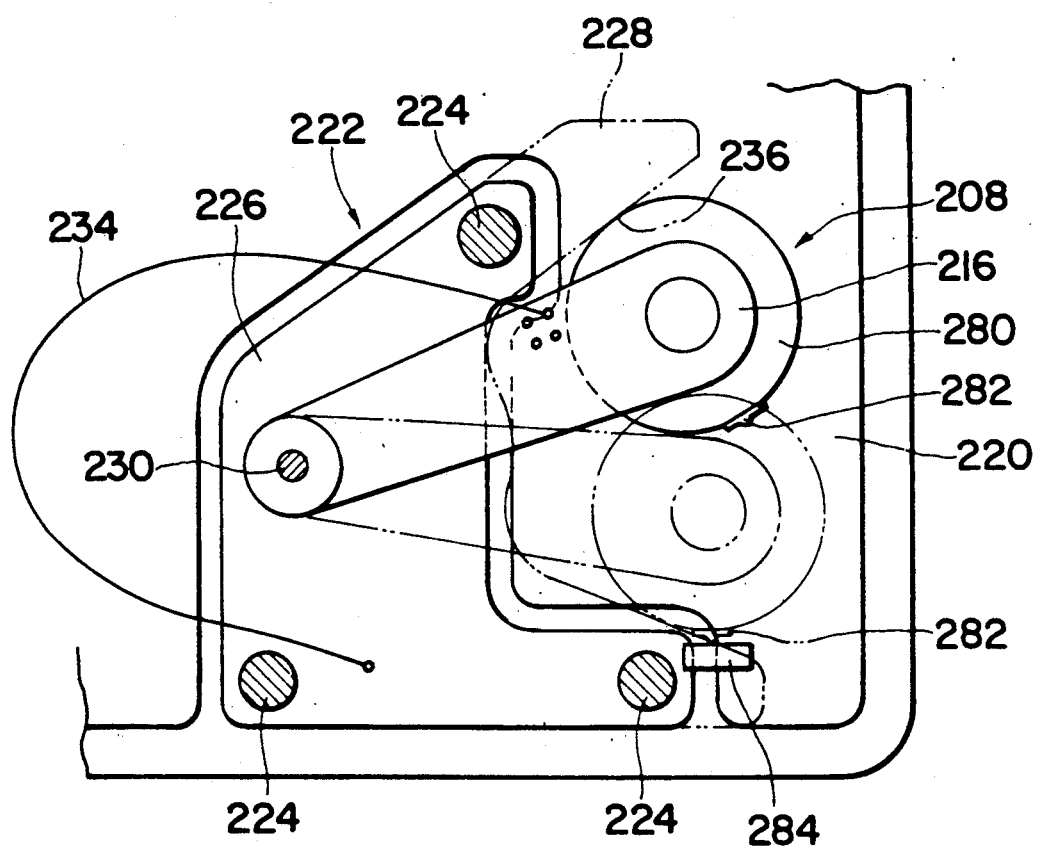
FIG. 15 is a front view showing a part of the inner structure of still another embodiment of the portable measuring apparatus of the present invention.

FIG. 15 shows a still another embodiment of the measuring apparatus of the present invention. This embodiment is a modification of the embodiment shown in FIG. 14. In this embodiment, a weight 280 is attached to an end of the arm 216 of the pendulum and a first metal contact element 282 is attached to the lower end of the weight 280. A second metal contact element 284 which contacts the first metal contact element 282 upon vibration of the pendulum 208 is provided in the vicinity of the lower stopper portion 238 of the substrate 220. Upon vibration of the pendulum 208, the first and second metal contact elements 282 and 284 are electrically connected, so that the contact signal is detected and the contact signal is transferred to the processing means 204. Thus, with this embodiment, the contact signal by each step can be detected.

The foregoing measuring apparatus of the present invention may be designed to include a measuring portion having the sensor 202 and the radio frequency transmitter of known for transmitting the contact signals and a separate display portion in which the processor 204 and the display 206 as well as a receiver for receiving contact signals from the transmitter are formed as one integral piece so as to measure the amount of exercise. In training for a marathon, race, for example, such measuring apparatus may be used as a pace-setting aid, if the measuring portion is attached to the waist of a runner and a coach holds the display portion.

Obviously, many modifications and variations of the present invention may be made by those skilled in the art without departing from the spirit and scope of the present invention, so that the scope of the invention should be interpreted not as limited to the particular methods or apparatus described in detail but only on the basis of the appended claims.

We claim:

1. An apparatus for measuring a walking speed of a walker, comprising:
   a detector detecting impacts made by contacts of a foot of the walker with the ground to produce corresponding contact signals;
   processing means for processing the contact signals from the detector, the processing means counting the number of the contact signals in a predetermined unit of time to obtain a pitch in said unit of time, calculating the stride of the walker from the obtained pitch and the height of the walker according to a predetermined empirical relationship, said height being inputted to the processing means beforehand, and multiplying the stride by the pitch to obtain a walking speed of the walker in said unit of time; and
   a display which displays the speed of the walker, wherein said empirical relationship is represented by the following equations:

$$ST = (0.1688 \times HT)/(1 - 0.0174 \times PI \times HT),$$

where
   ST is the stride in meters,
   PI is the pitch in number of steps every 10 seconds, and
   HT is the walker's height in meters,
   wherein said detector worn by the walker comprises a pendulum that swings due to an impact produced by contacting of a foot of the walker with the ground, a metallic ratchet gear rotated by said swinging of the pendulum, and magnet sensor means for sensing a motion of a serrated edge of the ratchet gear.

2. An apparatus for measuring a cumulative distance travelled by a walker, comprising the steps of:
   a detector detecting impacts made by contacts of a foot of the walker with the ground to produce corresponding contact signals;
   processing means for processing the contact signals from the detector, the processing means counting the number of the contact signals in a predetermined unit of time to obtain a pitch in said unit of time, calculating the stride of the walker from the obtained pitch and the height of the walker according to a predetermined empirical relationship, said height being inputted to the processing means beforehand, multiplying the stride by the pitch to obtain a walking speed of the walker in said unit of time, multiplying the walking speed by said unit of time to obtain the distance travelled by the walker in said unit of time, and integrating over a period of walking time the distance travelled by the walker in said unit of time to obtain a corresponding cumulative distance travelled by the walker; and
   a display which displays said cumulative distance, wherein said empirical relationship is represented by the following equations:

$$ST = (0.1688 \times HT)/(1 - 0.0174 \times PI \times HT),$$

where
   ST is the stride in meters,
   PI is the pitch in number of steps every 10 seconds, and
   HT is the walker's height in meters,
   wherein said detector worn by the walker comprises a pendulum that swings due to an impact produced by contacting of a foot of the walker with the ground, a metallic ratchet gear rotated by said swinging of the pendulum, and magnet sensor means for sensing a motion of a serrated edge of the ratchet gear.

3. An apparatus for measuring an amount of exercise in terms of cumulative energy consumed by a walker, comprising:
   a detector detecting impacts made by contacts of a foot of the walker with the ground to produce corresponding contact signals;
   processing means for processing the contact signals from the detector, the processing means counting the number of the contact signals in a predetermined unit of time to obtain a pitch in said unit of time, calculating the amount of energy consumed by the walker in said unit of time from said pitch and the weight of the walker according to a predetermined empirical relationship, said weight being provided to the processing means beforehand, and integrating the amount of energy consumed in said unit of time over time through the entire walking time to determine the corresponding cumulative consumption of energy; and
   a display which displays said cumulative consumption of energy, wherein said relationship is represented by the following equations:

$$C = (0.0005 \times PI \times WT)(\text{when } PI \leq 15)$$

$$C = (0.0013 \times PI - 0.0126) \times WT(\text{when } PI > 15)$$

where
   C is the consumed energy in kcal in 10 seconds,
   PI is the pitch in number of steps every 10 seconds, and
   WT is the bodyweight of the walker in kg,
   wherein said detector worn by the walker comprises a pendulum that swings due to an impact produced by contacting of a foot of the walker with the ground, a metallic ratchet gear rotated by said swinging of the pendulum, and magnet sensor means for sensing a motion of a serrated edge of the ratchet gear.

4. An apparatus for measuring a walking speed of a walker, comprising:
   a detector detecting impacts made by contacts of a foot of the walker with the ground to produce corresponding contact signals;
   processing means for processing the contact signals from the detector, the processing means counting the number of the contact signals in a predetermined unit of time to obtain a pitch in said unit of time, calculating the stride of the walker from the obtained pitch and the height of the walker according to a predetermined empirical relationship, said height being inputted to the processing means beforehand, and multiplying the stride by the pitch to obtain a walking speed of the walker in said unit of time; and
   a display which displays the speed of the walker, wherein said empirical relationship is represented by the following equations:

$$ST = (0.1688 \times HT)/(1 - 0.0174 \times PI \times HT),$$

where
ST is the stride in meters,
PI is the pitch in number of steps every 10 seconds, and
HT is the walker's height in meters,
wherein said detector worn by the walker comprises a pendulum that swings due to an impact produced by contacting of a foot of the walker with the ground, a magnet attached to an end of the pendulum and a reed switch for sensing a motion of the magnet.

5. An apparatus for measuring a cumulative distance travelled by a walker, comprising the steps of:
a detector detecting impacts made by contacts of a foot of the walker with the ground to produce corresponding contact signals;
processing means for processing the contact signals from the detector, the processing means counting the number of the contact signals in a predetermined unit of time to obtain a pitch in said unit of time, calculating the stride of the walker from the obtained pitch and the height of the walker according to a predetermined empirical relationship, said height being inputted to the processing means beforehand, multiplying the stride by the pitch to obtain a walking speed of the walker in said unit of time, multiplying the walking speed by said unit of time to obtain the distance travelled by the walker in said unit of time, and integrating over a period of walking time the distance travelled by the walker in said unit of time to obtain a corresponding cumulative distance travelled by the walker; and
a display which displays the speed of the walker, wherein said empirical relationship is represented by the following equations:

$$ST = (0.1688 \times HT)/(1 - 0.0174 \times PI \times HT),$$

where
ST is the stride in meters,
PI is the pitch in number of steps every 10 seconds, and
HT is the walker's height in meters,
wherein said detector worn by the walker comprises a pendulum that swings due to an impact produce by contacting of a foot f the walker with the ground, a magnet attached to an end of the pendulum and a reed switch for sensing a motion of the magnet.

6. An apparatus for measuring an amount of exercise in terms of cumulative energy consumed by a walker, comprising:
a detector detecting impacts made by contacts of a foot of the walker with the ground to produce corresponding contact signals;
processing means for processing the contact signals from the detector, the processing means counting the number of the contact signals in a predetermined unit of time to obtain a pitch in said unit of time, calculating the amount of energy consumed by the walker in said unit of time from said pitch and the weight of the walker according to a predetermined empirical relationship, said weight being provided to the processing means beforehand, and integrating the amount of energy consumed in said unit of time over time through the entire walking time to determined the corresponding cumulative consumption of energy; and
a display which displays said cumulative consumption of energy, wherein said relationship is represented by the following equations:

$$C = (0.0005 \times PI \times WT)(\text{when } PI \leq 15)$$

$$C = (0.0013 \times PI - 0.0126) \times WT(\text{when } PI > 15)$$

where
C is the consumed energy in kcal in 10 seconds,
PI is the pitch in number of steps every 10 seconds, and
WT is the bodyweight of the walker in kg,
wherein said detector worn by the walker comprises a pendulum that swings due to an impact produced by contacting of a foot of the walker with the ground, a magnet attached to an end of the pendulum and a reed switch for sensing a motion of the magnet.

7. An apparatus for measuring a walking speed of a walker, comprising:
a detector detecting impacts made by contacts of a foot of the walker with the ground to produce corresponding contact signals;
processing means for processing the contact signals from the detector, the processing means counting the number of the contact signals in a predetermined unit of time to obtain a pitch in said unit of time, calculating the stride of the walker from the obtained pitch and the height of the walker according to a predetermined empirical relationship, said height being inputted to the processing means beforehand, and multiplying the stride by the pitch to obtain a walking speed of the walker in said unit of time; and
a display which displays the speed of the walker, wherein said empirical relationship is represented by the following equations:

$$ST = (0.1688 \times HT)/(1 - 0.0174 \times PI \times HT),$$

where
ST is the stride in meters,
PI is the pitch in number of steps every 10 seconds, and
HT is the walker's height in meters,
wherein said detector worn by the walker comprises a pendulum that swings due to an impact produced by contacting of a foot of the walker with the ground, a magnet attached to an end of the pendulum and magnet sensor means for sensing a motion of the magnet.

8. An apparatus for measuring a cumulative distance travelled by a walker, comprising the steps of:
a detector detecting impacts made by contacts of a foot of the walker with the ground to produce corresponding contact signals;
processing means for processing the contact signals from the detector, the processing means counting the number of the contact signals in a predetermined unit of time to obtain a pitch in said unit of time, calculating the stride of the walker from the obtained pitch and the height of the walker according to a predetermined empirical relationship, said height being inputted to the processing means beforehand, multiplying the stride by the pitch to obtain a walking speed of the walker in said unit of time, multiplying the walking speed by said unit of time to obtain the distance travelled by the walker in said unit of time, and integrating over a period of walking time the distance travelled by the walker in aid unit of time to obtain a corresponding cumulative distance travelled by the walker; and a display which displays the speed of the walker, wherein said empirical relationship is represented by the following equations:

$$ST = (0.1688 \times HT)/(1 - 0.0174 \times PI \times HT),$$

where
ST is the stride in meters,
PI is the pitch in number of steps every 10 seconds, and
HT is the walker's height in meters,
wherein said detector worn by the walker comprises a pendulum that swings due to an impact produced by contacting of a foot of the walker with the ground, a magnet attached to an end of the pendulum and magnet sensor means for sensing a motion of the magnet.

9. An apparatus for measuring an amount of exercise in terms of cumulative energy consumed by a walker, comprising:

a detector detecting impacts made by contacts of a foot of the walker with the ground to produce corresponding contact signals;

processing means for processing the contact signals from the detector, the processing means counting the number of the contact signals in a predetermined unit of time to obtain a pitch in said unit of time, calculating the amount of energy consumed by the walker in said unit of time from said pitch and the weight of the walker according to a predetermined empirical relationship, said weight being provided to the processing means beforehand, and integrating the amount of energy consumed ins aid unit of time over time through the entire walking time to determine the corresponding cumulative consumption of energy; and a display which displays said cumulative consumption of energy, wherein said relationship is represented by the following equations:

$$C = (0.0005 \times PI \times WT)(\text{when } PI \leq 15)$$

$$C = (0.0013 \times PI - 0.0126) \times WT(\text{when } PI > 15)$$

where
C is the consumed energy in kcal in 10 seconds,
PI is the pitch in number of steps every 10 seconds, and
WT is the bodyweight of the walker in kg,
wherein said detector worn by the walker comprises a pendulum that swings due to an impact produced by contacting of a foot of the walker with the ground, a magnet attached to an end of the pendulum and magnet sensor means for sensing a motion of the magnet.

10. An apparatus for measuring a walking speed of a walker, comprising:

a detector detecting impacts made by contacts of a foot of the walker with the ground to produce corresponding contact signals;

processing means for processing the contact signals from the detector, the processing means counting the number of the contact signals in a predetermined unit of time to obtain a pitch in said unit of time, calculating the stride of the walker from the obtained pitch and the height of the walker according to a predetermined empirical relationship, said height being inputted to the processing means beforehand, and multiplying the stride by the pitch to obtain a walking speed of the walker in said unit of time; and a display which displays the speed of the walker, wherein said empirical relationship is represented by the following equations:

$$ST = (0.1688 \times HT)/(1 - 0.0174 \times PI \times HT),$$

where
ST is the stride in meters,
PI is the pitch in number of steps every 10 seconds, and
HT is the walker's height in meters,
wherein said detector worn by the walker comprises a pendulum that swings due to an impact produced by contacting of a foot of the walker with the ground, a first metal contact element attached to an end of the pendulum and a second metal contact element which contacts said first metal contact element upon swinging of the pendulum.

11. An apparatus for measuring a cumulative distance travelled by a walker, comprising the steps of:

a detector detecting impacts made by contacts of a foot of the walker with the ground to produce corresponding contact signals;

processing means for processing the contact signals from the detector, the processing means counting the number of the contact signals in a predetermined unit of time to obtain a pitch in said uint of time, calculating the stride of the walker from the obtained pitch and the height of the walker according to a predetermined empirical relationship, said height being inputted to the processing means beforehand, multiplying the stride by the pitch to obtain a walking speed of the walker in said unit of time, multiplying the walking speed by said unit of time to obtain the distance travelled by the walker in said unit of time, and integrating over a period of walking time the distance travelled by the walker in said unit of time to obtain a corresponding cumulative distance travelled by the walker; and a display which displays the speed of the walker, wherein said empirical relationship is represented by the following equations:

$$ST = (0.1688 \times HT)/(1 - 0.0174 \times PI \times HT),$$

where
ST is the stride in meters,
PI is the pitch in number of steps every 10 seconds, and
HT is the walker's height in meters,
wherein said detector worn by the walker comprises a pendulum that swings due to an impact produced by contacting of a foot of the walker with the ground, a first metal contact element attached to an end of the pendulum and a second metal contact element which contacts said first metal contact element upon swinging of the pendulum.

12. An apparatus for measuring an amount of exercise in terms of cumulative energy consumed by a walker, comprising:
- a detector detecting impacts made by contacts of a foot of the walker with the ground to produce corresponding contact signals;
- processing means for processing the contact signals from the detector, the processing means counting the number of the contact signals in a predetermined unit of time to obtain a pitch in said unit of time, calculating the amount of energy consumed by the walker in said unit of time from said pitch and the weight of the walker according to a predetermined empirical relationship, said weight being provided to the processing means beforehand, and integrating the amount of energy consumed in said unit of time over time through the entire walking time to determine the corresponding cumulative consumption of energy; and
- a display which displays said cumulative consumption of energy, wherein said relationship is represented by the following equations:

$$C = (0.0005 \times PI \times WT) \text{(when } PI \leq 15\text{)}$$

$$C = (0.0013 \times PI - 0.0126) \times WT \text{(when } PI > 15\text{)}$$

where
C is the consumed energy in kcal in 10 seconds,
PI is the pitch in number of steps every 10 seconds, and
WT is the bodyweight of the walker in kg,
wherein said detector worn by the walker comprises a pendulum that swings due to an impact produced by contacting of a foot of the walker with the ground, a first met contact element attached to an end of the pendulum and a second metal contact element which contacts said first metal contact element upon swinging of the pendulum.

* * * * *